United States Patent [19]
Berkelaar

[11] Patent Number: 5,860,995
[45] Date of Patent: Jan. 19, 1999

[54] LAPAROSCOPIC ENDOSCOPIC SURGICAL INSTRUMENT

[75] Inventor: Gerald Berkelaar, Norwell, Mass.

[73] Assignee: Misener Medical Co. Inc., Norwell, Mass.

[21] Appl. No.: 729,633

[22] Filed: Sep. 23, 1996

Related U.S. Application Data

[60] Provisional application No. 60/004,124 Sep. 22, 1995.
[51] Int. Cl.$^6$ ...................................................... A61B 17/32
[52] U.S. Cl. ........................................... 606/174; 606/208
[58] Field of Search ................................ 606/1, 106, 107, 606/127, 151, 167, 170, 171, 174, 205–211

[56] References Cited

U.S. PATENT DOCUMENTS 5,350,391 9/1994 Iacovelli .................................. 606/174
5,454,827 10/1995 Aust et al. ............................... 606/205

Primary Examiner—Glenn K. Dawson
Attorney, Agent, or Firm—John M. Brandt

[57] ABSTRACT

An improved laparoscopic surgical instrument having a proximal control end and a distal surgical instrument end adapted for performing medical procedures through the abdominal wall wherein the surgical instrument is arranged to articulate in a selected plane a full 180 degrees. Actuation of the articulating mechanism is provided by a pair of cables attached to a rotatable cable control whereby rotation of the rotatable cable control draws one cable toward the control handle while simultaneously releasing the other. The distal end of each cable is attached to an opposite side of the surgical instrument which is free to rotate about a pivot in the articulation plane when pulled upon by one of the cables. The cables pass on opposite sides of the pivot allowing for 90 degree rotations each side of the central axis of the instrument.

10 Claims, 7 Drawing Sheets

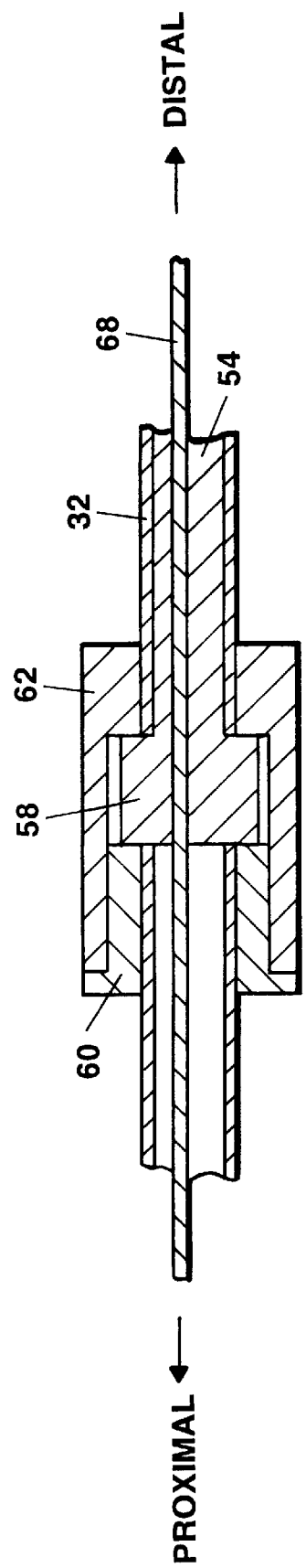
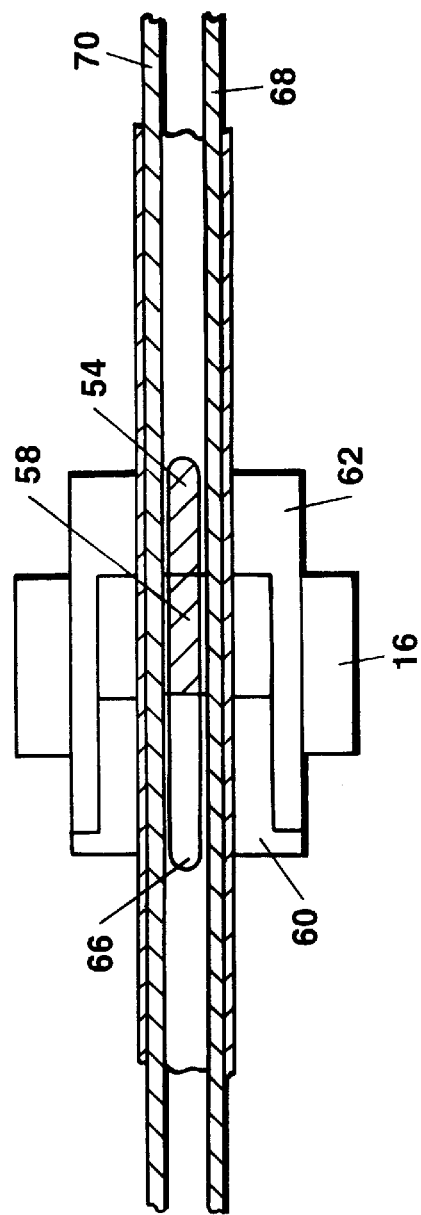
*Figure 3*
*Figure 3a*

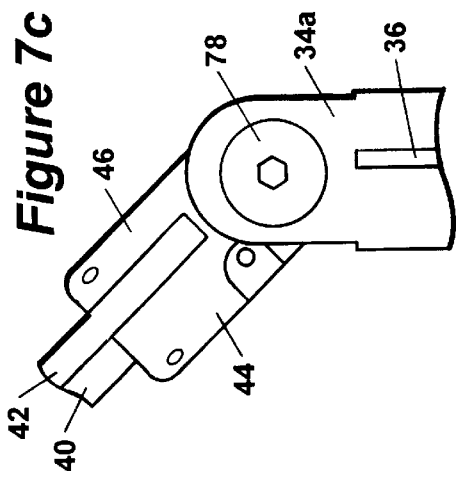
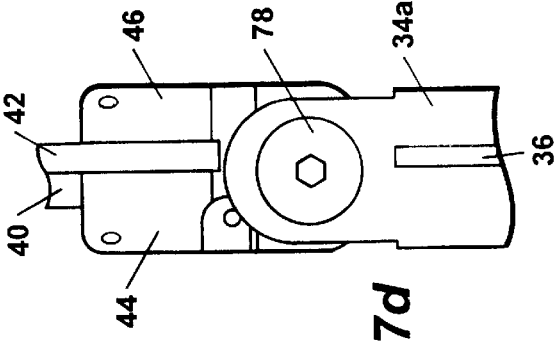
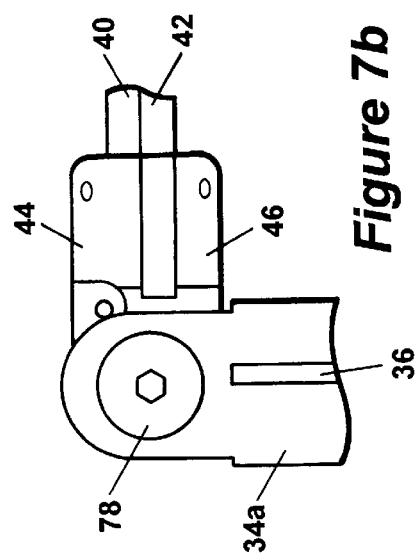
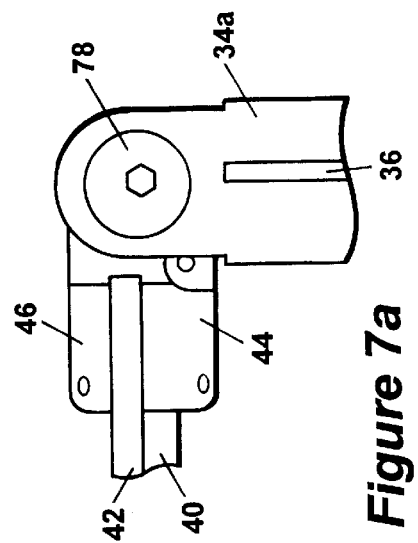

LAPAROSCOPIC ENDOSCOPIC SURGICAL INSTRUMENT

This application claims benefit of U.S.C. Provisional Appl. Ser. No. 60/004,124 filed Sep. 22, 1995.

BACKGROUND OF THE INVENTION

1. Field of the Invention

The invention resides in the field of surgical apparatus and more particularly relates to instruments for performing laparoscopic and endoscopic surgical procedures having an end portion capable of articulated or pivotal movement within a patient's body.

2. Description of the Prior Art

Minimally invasive surgery (MIS) has, in recent years, become important in hospitals and surgical centers. In MIS procedures, small incisions are made in the patient's body to provide access for various surgical devices for viewing and operating inside the patient. Using specially designed instruments such as a laparoscope or endoscope, trained surgeons can see directly inside the human body and perform operations using specially designed laparoscopic surgical instruments. Laparoscopic surgical instruments include scissors, dissectors, graspers and retractors. These instruments generally consist of a handle which remains outside of the patient's body and which is used by the surgeon to control the operation of the instrument, an elongated tubular section which fits through a tube or trocar device entering the patient's body, and a distal tip used to execute the particular procedure.

Many examples of MIS instrumentation exist in the prior art. Some early instruments were essentially elongated scalpels or probes. Early instruments with handles permitted opening and closing of the distal tip elements. Somewhat later instruments came to have axis rotation as a common feature. Axis rotation gave surgeons increased flexibility in the positioning of the elements of the distal tip.

A continuing limitation for surgeons has been the lack of flexibility of these instruments through the tubular section to the distal tip elements. To cope with the limitations of these instruments, surgeons may operate in teams with the instruments handed back and forth from surgeon to surgeon across the patient. Inability to reach around nerves and blood vessels may cause surgeons to resort to open surgery instead of continuing with a MIS procedure. By providing an easily manipulated, fully articulating distal tip, this invention increases the flexibility of laparoscopic surgical instruments, enabling surgeons to operate more safely, more quickly and efficiently, and with decreased risk to the patient.

An example of an endoscopic surgical instrument is illustrated in U.S. Pat. No. 2,113,246, Wappler. This patent discloses endoscopic forceps comprising an elongated conduit with jaws at the distal end thereof, a control rod in the conduit for controlling the operation of the jaws, and a control handle at the proximal end of the conduit which is operatively connected to the control rod.

Improvements have been made in the art of surgical instruments to increase their range of operability. For example, U.S. Pat. No. 4,763,669, Jaeger, discloses a micro-surgery instrument with an adjustable angle of operation for obtaining cervical biopsies.

Similarly, U.S. Pat. No. 4,880,015, Nierman, discloses a surgical device having an increased range of operability. In particular, this patent shows a biopsy forceps designed for use through a flexible fiber optic bronchoscope. The biopsy forceps includes a handle connected to a thin elongated flexible shaft with a distal portion thereof hinged to the shaft. A grasping tool or biopsy forceps is attached to the distal hinged portion. Control wires extend from the handle to the distal end to the shaft for controlling the angular rotation of the distal portion of the instrument.

Further, U.S. Pat. No. 5,350,391 Iacovelli discloses a device having a pair of handles which may be operated in tandem to effect the orientation of a surgical instrument in a variety of positions.

Also of note is U.S. Pat. No. 5,330,502, Hassler et al., describing a mechanism utilizing a combination of a tube and knob to effect articulation of from zero to 90 degrees.

Similarly, U.S. Pat. No. 5,383,888 Boris Zvenyatsky, et al., discloses an endoscopic surgical instrument with rotation, electrocautery, and a limited 90-degree articulation achieved through linkages.

None of the instruments described above is flexible enough to address the wide range of requirements for surgical procedures performed internally to the patient's body. Further, none of the instruments described permits the surgical team to proceed as quickly and efficiently as would be desired under normal operating conditions. The instruments described lack the ability to rotate the distal tip about the longitudinal axis of the instrument while fully articulating the tip to any setting relative to the tubular section of the instrument. This lack of flexibility requires surgeons to manually rotate and move the instrument relative to the patient body to perform the procedure. In some cases the instruments described cannot perform the procedure due to the location of blood vessels and blocking tissues.

Accordingly it is an object of this invention to provide laparoscopic surgical instruments having a distal tip independently moveable about the two axis of rotation relative to the handle while the instrument is in use, giving greatly expanded flexibility to the surgeon for motion inside the patient body.

It is another object of this invention to provide a surgical instrument capable of supporting a variety of tool heads with frill motion capability. Individual heads may be used to cut, grasp, push, pull probe, electrocauterize, and perform other actions either singly or in combination.

It is another object of this invention to provide a light-weight laparoscopic surgical instrument which enables the surgeon to reach under and around both tissue and blood vessels during an operation.

It is a further object of this invention is to provide a laparoscopic surgical instrument of simplified and rugged construction which is inexpensive to manufacture relative to both disposable and reusable instruments in current use.

These and other objects of the invention will be more fully understood from the summary which follows.

SUMMARY OF THE INVENTION

The invention may be summarized as an improved laparoscopic surgical instrument having an articulating distal tip which is easily and convenient to manipulate. By "fully articulating" is meant the ability to move the tip from side to side a complete semi circle, i.e., 180 degrees. This is accomplished by the use of a pair of cables one each on either side of the shaft or bar to which the surgical instrument is pivotally attached. The cables extend back to the proximal end or handle wherein a rotatable cable control is mounted. The control is arranged to release the tension on one cable while pulling on the other and is free to move through as many degrees of rotation as are needed to effect the desired amount of articulation.

In the preferred embodiment a drum mounted on an axis perpendicular to the longitudinal axis of the instrument shaft is positioned atop the handle and is operable by a thumb wheel. The cables pass on either side of the drum and are held in position by for example, tension adjusting set screws.

The extended articulating range provided by the aforementioned rotatable cable control may be augmented by one or more yokes for mounting the surgical instrument at the distal end. The instrument is secured between the arms of the yoke and may be arranged to pivot about an axis between the arms as well. This is particularly useful when the instrument in question is a scissors wherein a yoke may be provided for each blade further providing secure points of attachment for the ends of the articulating cables.

Provision for activating the surgical instrument where required, for example, when the instrument is a scissors, is provided by a handle operated push rod. Electrocautery is also made possible by enabling a connection of an external power source to the internal elements of the surgical instrument with power transmission through the shaft and useable at the distal tip.

The description of the preferred embodiment and drawings below will clarify these and other features and advantages of the invention.

DESCRIPTION OF THE DRAWINGS

FIG. 2a is a cross sectional view of another portion of the embodiment of FIG. 1;

FIG. 3 is a cross sectional side view of a portion of FIG. 2;

FIG. 3a is a cross sectional top view of a portion of FIG. 2;

FIG. 4 is a cross sectional side view of a portion of FIG. 2a;

FIG. 4a is a cross sectional top view of a portion of FIG. 2a;

FIG. 5 is a perspective view of the embodiment illustrated in FIG. 2a;

FIG. 6 is a cross sectional side view of the rear portion of FIG. 2;

FIGS. 7a, 7b, 7c and 7d illustrate a portion of the invention in various positions.

DESCRIPTION OF THE PREFERRED EMBODIMENT

Figure 1:
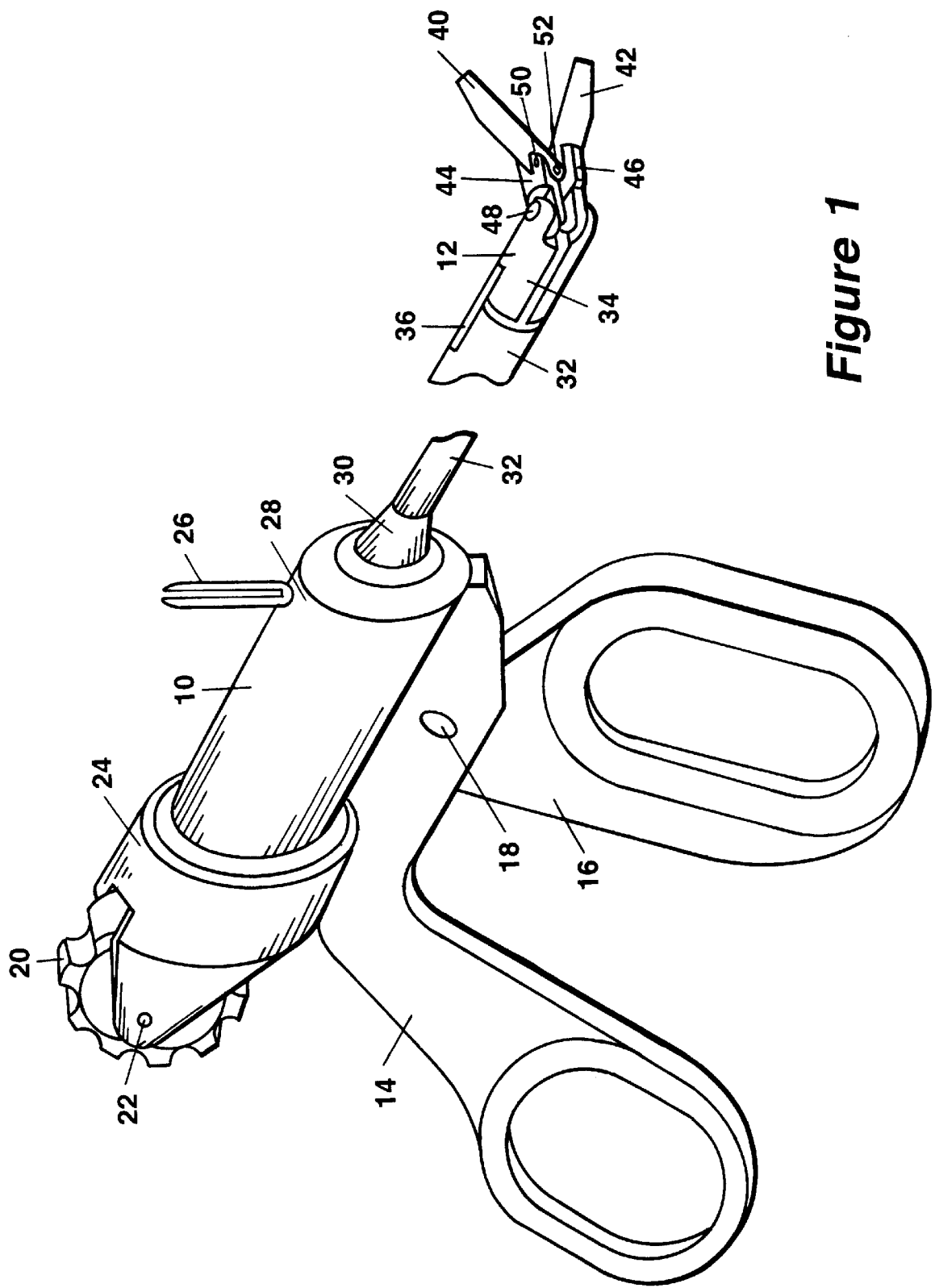
FIG. 1 is a perspective view of the preferred embodiment of the invention.

Referring first to FIG. 1, there is illustrated a perspective view of the preferred embodiment of the invention comprising proximal control mechanism end 10 and distal surgical instrument end 12. Proximal control mechanism end 10 consists of a handle body 14, a trigger handle 16 which is mounted on and rotates about trigger handle pivot pin 18, an instrument articulation control thumb wheel 20 rotatably mounted on pivot pin 22 and an instrument rotation sleeve 24. An electrocautery connection pin 26 is mounted atop housing 28 which terminates in trocar adapter 30. Shaft 32 connects proximal end 10 and distal end 12 and in use extends through the patients body providing a conduit for the articulation control cables to be described below. The shaft may be rotated to alter the orientation of the distal end by rotation of sleeve 24.

Distal surgical instrument end 12, shown somewhat enlarged for purposes of clarity consists of pivot bar 34 attached to shaft 32 by hinge 36 and surgical instrument 38 formed of scissor blades 40 and 42 pivotally mounted on yokes 44 and 46 respectively. Yokes 44 and 46 are pivotally mounted on bar 34 by pivot 48. A cable receiving hole 50 is formed in yoke 44 and another not shown is formed on the opposite side of yoke 46. Blades 40 and 42 mutually open and close by pivoting about pivot 52.

Figure 2:
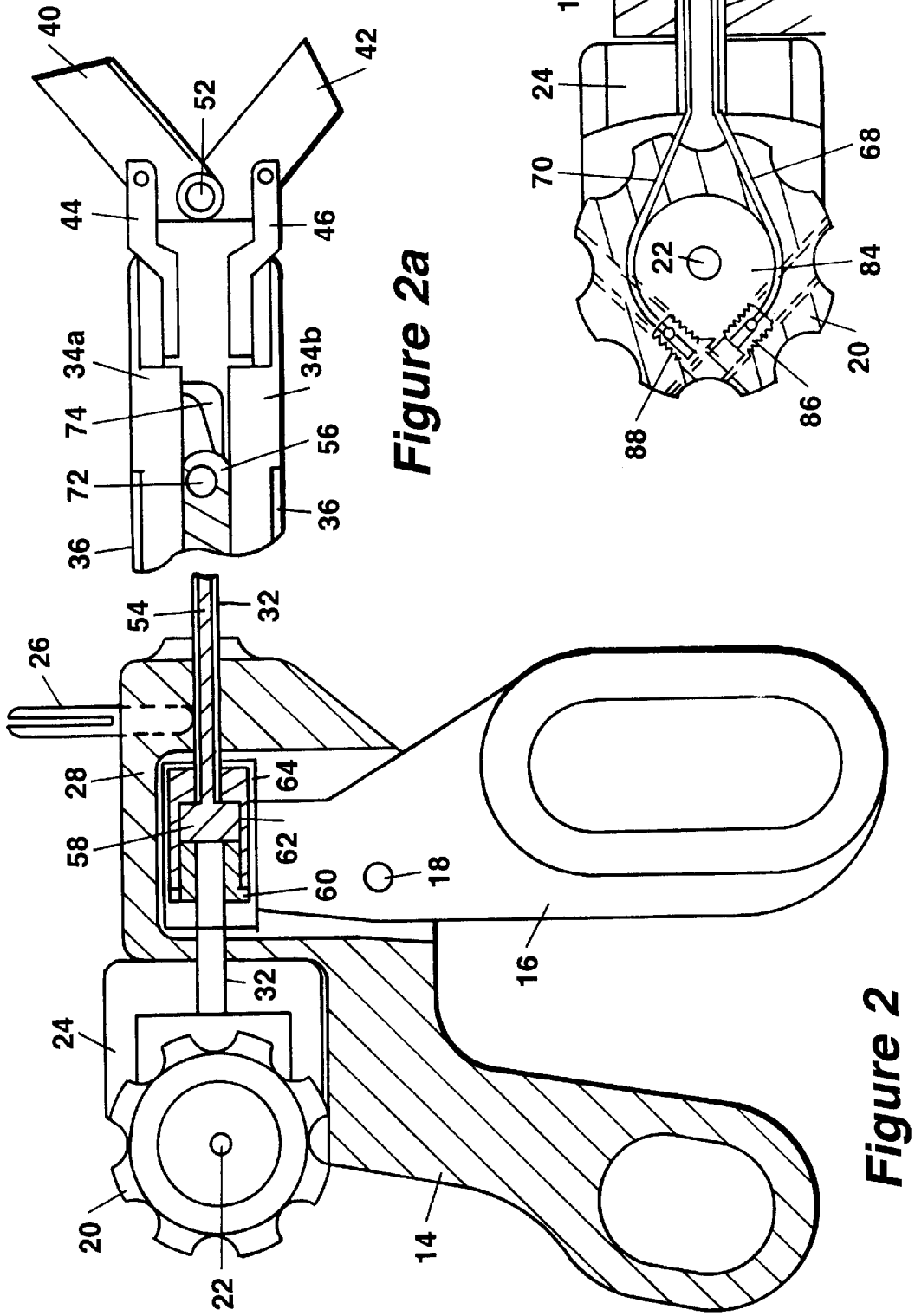
FIG. 2 is a cross sectional side view of a portion of the embodiment of FIG. 1.

Referring next to FIGS. 2 and 2a cross sectional side views of the embodiment of FIG. 1 are shown. In addition to the components previously described, the mechanism for actuating i.e., opening an closing, scissors blades 40 and 42 is illustrated.

Shaft 32 is hollow and contains push rod 54 terminating in distal tip 56. The proximal end terminates in tab 58 which is held between circular bushing pair 60 and 62 and is free to move in a slot in shaft 32. The bushing pair is attached to handle 16 and is free to move in cavity 64. Thus at the proximal end back and forth motion of handle 16 translates into back and forth motion of push rod 54 in shaft 32.

Reference is now made to FIGS. 3 and 3a wherein is illustrated an enlarged side and top view of the sub assembly described above showing slot 66 and articulating control cables 68 and 70 to be described in greater detail below.

Pivot bar 34 is a compound structure consisting of a pair of push rod cam followers 34a and 34b. Each is attached to shaft 32 by a bar of flexible metal 36 which constitutes a living hinge, that is a structure which bends in response to pressure without undue resistance and without breaking or cracking over a reasonable period of time. A suitable material is sold under the trade name NITINOL, a shape memory metal, available from Nitinol Development Co.

Figure 4:
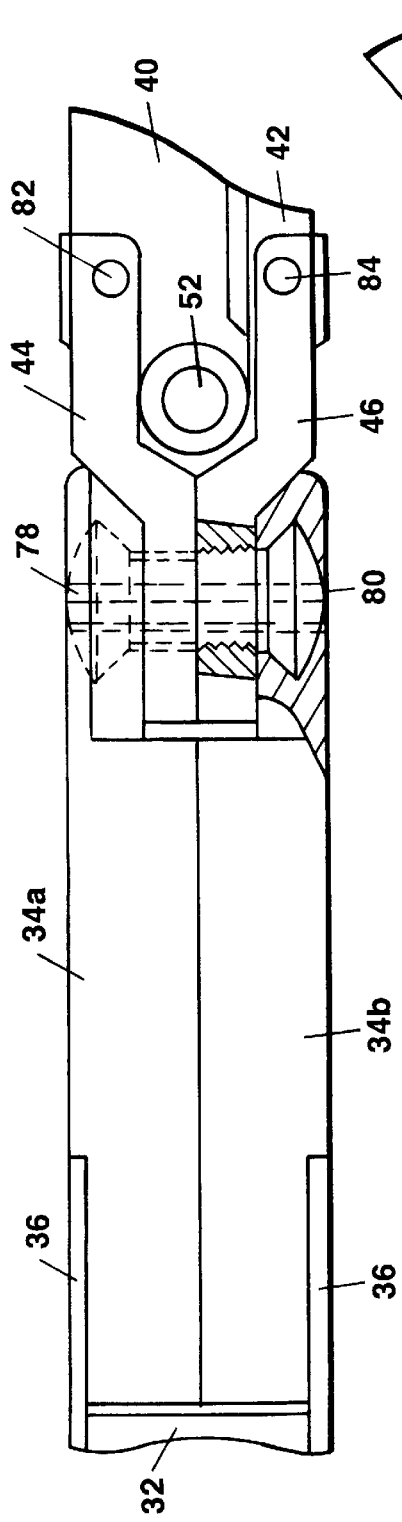
Figure 4A:
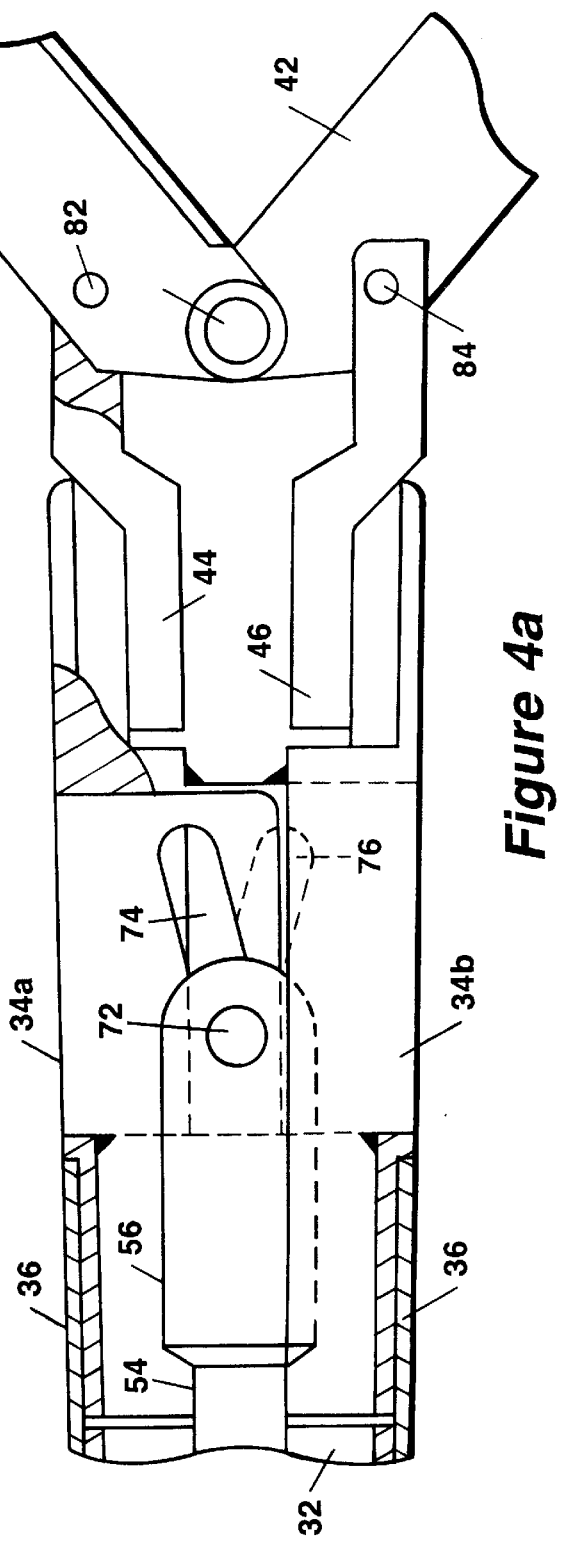

As is clearly shown in FIG. 4a push rod tip 56 is bifurcated and has pin 72 laterally disposed there through. Pin 72 passes through canted slots 74 and 76 disposed in followers 34a and 34b respectively. As rod 54 and tip 56 are propelled forward by the motion of handle 16 followers 34a and 34b will lift upwards on hinges 36 in response to the pressure of pin 72 on the sides of slots 74 and 76.

Attached to each follower is a yoke 44 and 46 each attached in turn to a scissors blade 40 and 42. The yokes are pivotally attached to the followers by pivots 78 and 80 and to the blades by pivots 82 and 84. The combination illustrated will then function to open the scissors blades 40 and 42 about pivot 52 on the forward motion of rod 54 as shown in FIG. 4a and close the blades upon the withdrawal of rod 54 as shown in FIG. 4.

Figure 5:
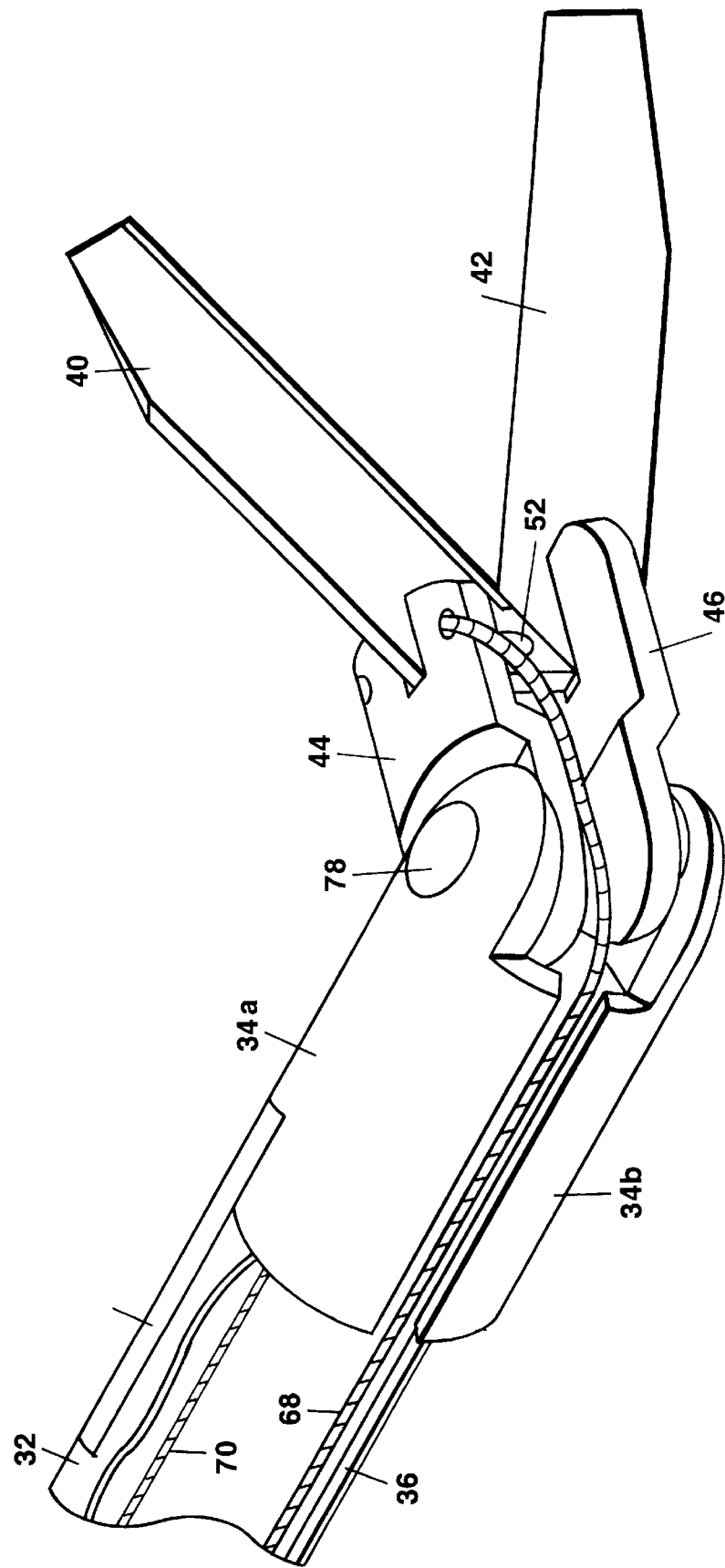

FIG. 5 is a perspective view of the above described assembly shown articulated to the left by the pull of cable 70 and the release of cable 68 by operation of the rotatable cable control via thumb wheel 20. Also illustrated are the scissors blades 40 and 42 in an open position prior to retraction of rod 54 by handle 16 wherein the components are in the relationship and position shown in FIG. 4a.

Referring next to FIG. 6, a cross sectional side view of the rotatable cable control assembly is shown in which drum 84 rotationally operated by thumb wheel 20 has cables 68 and 70, extending through shaft 32 from the distal to the proximal ends, secured by set screws 86 and 88 respectively. As illustrated, the cables are partially wrapped around drum 84 on opposite sides to provide for the simultaneous pull and release of each cable depending upon the direction of rotation. It will be seen that this arrangement provides great latitude in the distance the cables may be moved thereby providing the extended articulation range described above.

This range is more filly illustrated in FIGS. 7a, 7b, 7c and 7d wherein various articulated positions of the distal end are shown. FIG. 7a shows articulation 90 degrees to the left; 7b 90 degrees to the right; 7c 45 degrees to the left; and 7d zero degrees.

Figure 8:
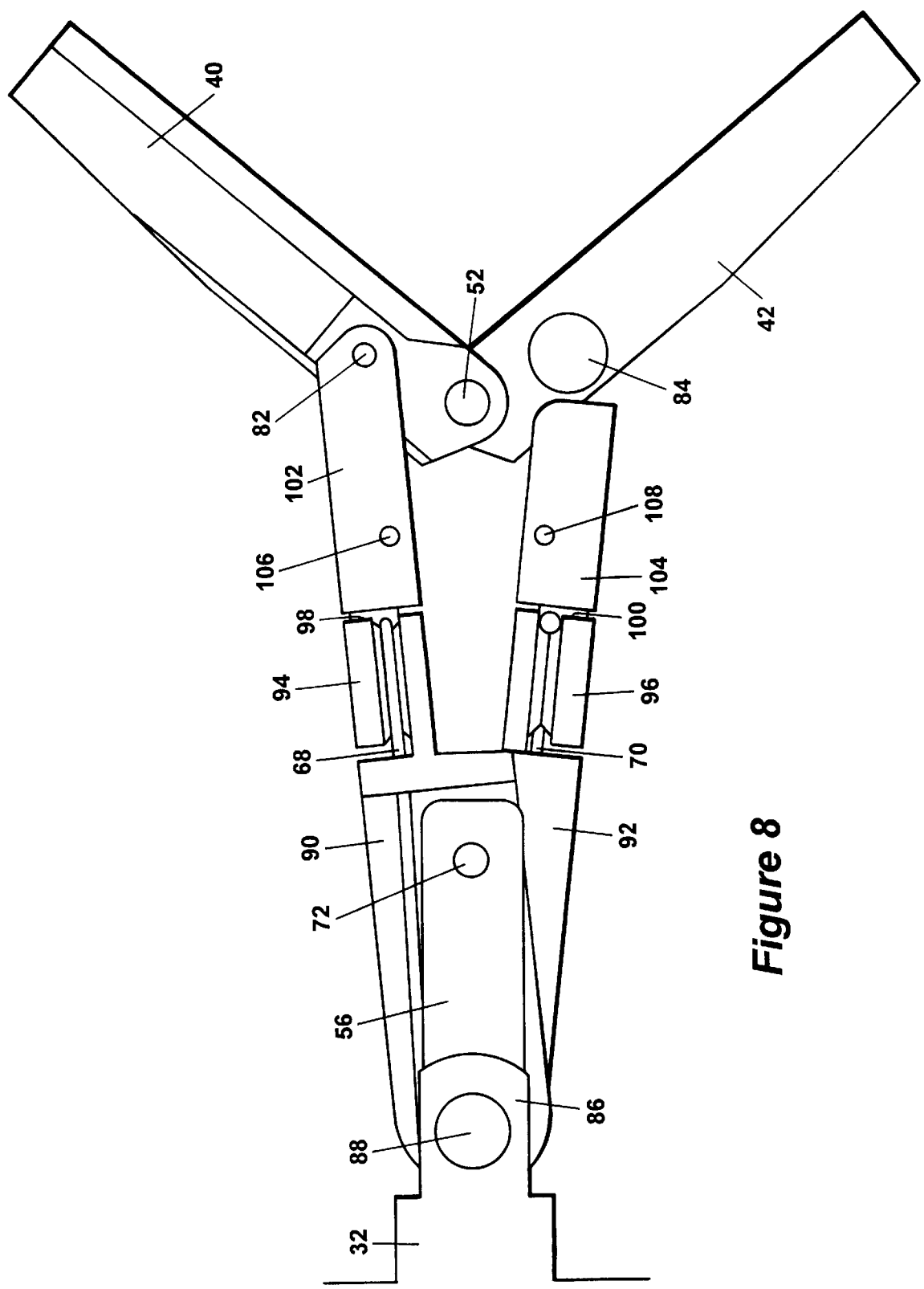
FIG. 8 is a side view of an alternative embodiment of a portion of the preferred embodiment.

Referring finally to FIG. 8, an alternative structure for the operation, i.e., opening and closing of scissor blades 40 and 42 is illustrated. Like numbers refer to like parts where ever possible. Shaft 32 has bifurcated end 86 through which is placed pivot 88 about which push rod cam follows 90 and 92 are rotatable mounted. Push rod distal tip 56 again has pin 72 engaging canted slots not shown for spreading and closing follows 90 and 92 upon the back and forth motion of push rod 54. Each follower has a turret 94 and 96 attached thereto for securing and guiding cables 68 and 70. The turrets have extensions 98 and 100 which slide into slots in yokes 102 and 104 and are held in place by locking pins 106 and 108. The yokes in turn attach to blades 40 and 42 by pins 82 and 84. As will be seen the above described alternative replaces living hinges 36 with pivot 88 as the common pivot mechanism for effecting the operation of the scissors pair 40 and 42.

Certain modifications of the above described embodiments of the invention will now be obvious to those skilled in the art without departing from the spirit and intent of the disclosure. Accordingly the scope of the invention is defined by the following claims.

What is claimed is:

1. In a laparoscopic surgical instrument having an elongated shaft; a proximal control mechanism at a proximal end and a distal surgical instrument arranged to be pivotally mounted at the opposite distal end, means for articulating said instrument 90 degrees either side of the central axis of said shaft in a selected plane comprising:
   a. a pivot bar mounted on said shaft at said distal end for pivotally mounting said instrument;
   b. a first cable attached to one side of said instrument extending to said proximal end on one side of said pivot bar;
   c. a second cable attached to the opposite side of said instrument extending to said proximal end on the opposite side of said pivot bar; and
   d. rotatable cable control means for alternately pulling each of said cables through said shaft toward said proximal end while simultaneously releasing the opposite cable to effect articulation of said instrument 90 degrees either side of the central axis of said shaft wherein said control means comprise a rotatable drum mounted at said proximal end and wherein each of said first and second cables is wound at least in part about said drum in opposite direction.

2. The apparatus of claim 1 wherein each of said first and second cables is attached to said drum by set screw means.

3. The apparatus of claim 1 wherein said drum is rotatable by a thumb wheel mounted at said proximal end.

4. The apparatus of claim 1, wherein said instrument comprises a yoke pivotally mounted on said pivot bar and wherein said cables are attached to opposite sides of said yoke.

5. The apparatus of claim 1 wherein said instrument comprises a scissors and further includes
   a. a first yoke pivotally mounted on said bar and attached to one blade of said scissors;
   b. a second yoke pivotally mounted on said bar and attached to the other blade of said scissors; and wherein said first cable is attached to said first yoke and said second cable is attached to said second yoke.

6. In a laparoscopic surgical instrument having an elongated shaft; a proximal control mechanism at a proximal end and a distal surgical instrument comprising a scissors having first and second mutually pivotable blades arranged to be pivotally mounted at the opposite end, means for opening and closing said blades comprising
   a. a push rod slidably mounted within said shaft, said rod reciprocally operated from said proximal end, said rod having a distal tip;
   b. a push rod pin laterally disposed in the distal tip of said rod; and
   c. first and second blade operating members each having a proxomal end and a distal end and each pivotally attached to one of said blades and disposed in side by side relationship on either side of said distal tip, each of said members hingeably attached to the distal end of said shaft, each of said members having a slot for receiving said push rod pin, each of said slots canted in an opposite direction transverse said members whereby motion in one direction of said push rod forces said members and said blades apart and motion of said rod in the opposite direction draws said members and said blades together.

7. The apparatus of claim 6 wherein said blade operating members and said shaft are hingeably attached by a living hinge.

8. The apparatus of claim 6 wherein said blade operating members and said shaft are hingeably attached by a pivot extending through said member and said shaft perpendicular to the longitudinal axis of said shaft.

9. The apparatus of claim 6 wherein said distal end of each of said blade operating members is bifucated forming a yoke surrounding each of said scissor blades at the pivotal point of attachment.

10. The apparatus of claim 6 further including a pair of cables one each attached to each blade operating member, said cables arranged to extend through said shaft to said proximal end on opposite sides of said push rod pin and wherein said proximal control mechanism comprises a rotatable cable control for simultaneously pulling one cable and releasing the other to effect side to side articulation of said instrument.

* * * * *